United States Patent [19]
Torii et al.

[11] Patent Number: 5,905,147
[45] Date of Patent: May 18, 1999

[54] PROCESS FOR PREPARING β-LACTAM COMPOUND

[75] Inventors: Sigeru Torii, Okayama-ken; Hideo Tanaka, Oakayama; Michio Sasaoka; Yutaka Kameyama, both of Tokushima, all of Japan

[73] Assignee: Otsuka Kagaku Kabushiki Kaisha, Osaka-Fu, Japan

[21] Appl. No.: 08/732,443

[22] PCT Filed: Mar. 7, 1996

[86] PCT No.: PCT/JP96/00549

§ 371 Date: Nov. 6, 1996

§ 102(e) Date: Nov. 6, 1996

[87] PCT Pub. No.: WO96/28422

PCT Pub. Date: Sep. 19, 1996

[30] Foreign Application Priority Data

Mar. 10, 1995 [JP] Japan .................................. 7-079485
Mar. 10, 1995 [JP] Japan .................................. 7-079486

[51] Int. Cl.[6] ............... C07D 205/08; C07D 499/06; C07B 39/00
[52] U.S. Cl. ............................................. 540/358
[58] Field of Search ................................. 540/358

[56] References Cited

FOREIGN PATENT DOCUMENTS

| 529081 | 3/1993 | European Pat. Off. . |
| 49-82691 | 8/1974 | Japan . |
| 60-149590 | 8/1985 | Japan . |
| 4-211055 | 8/1992 | Japan . |
| 4-283584 | 10/1992 | Japan . |
| 4-295484 | 10/1992 | Japan . |
| 5-97864 | 4/1993 | Japan . |
| 6-2183 | 1/1994 | Japan . |
| 7-61967 | 3/1995 | Japan . |

OTHER PUBLICATIONS

Chemistry Letters,(8) 709–710 1995–Tanaka et al.
Bull. Chem. Soc. Jpn., 68 (5) 1385–1391 1995–Tanaka et al.

*Primary Examiner*—Mark L. Berch
*Attorney, Agent, or Firm*—Nikaido Marmelstein Murray & Oram LLP

[57] ABSTRACT

The present invention provides a process for producing a β-lactam halide compound represented by the general formula (2) which process is characterized in that the hydroxyl group of a β-lactam halide compound represented by the general formula (1) is substituted with a halogen atom or a leaving group.

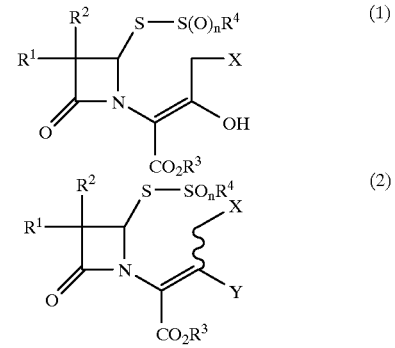

6 Claims, No Drawings

PROCESS FOR PREPARING β-LACTAM COMPOUND

This application is a 371 of PCT/JP96/00549 filed Mar. 07, 1996.

TECHNICAL FIELD

The present invention relates to a process for preparing β-lactam halide compounds which are useful as intermediates of antibacterial agents having a cephalosporin skeleton with no carbon atom attached to its 3-position (JP-A-135859/1983). The invention relates also to a process for preparing an exo- methylenepenam compound from the β-lactam halide compound.

The exo-methylenepenam compound of the present invention is an important intermediate for synthesizing, for example., β-lactamase inhibitor (Bawldwin et al, J. Chem. Soc., Chem. Commun., 1987, 81, S. Torii et al., Antibit. Chem. Lett., 1993, 3, 2253).

BACKGROUND ART

The β-lactam halide compound of the invention represented by the general formula (2) is prepared by reacting halogen molecules with an allenyl β-lactam compound represented by the general formula (3) as is already known (Can. J. Chem., 1978, 56, 1335). However, this process affords a mixture of α, β- and β, τ-position isomers depending on the kind of halogen molecule and is not usable in actuality. This process further gives the product via an unstable allene compound as an intermediate and therefore involves many problems on an industrial scale.

(3)

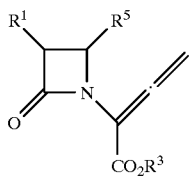

wherein $R^1$ and $R^3$ are as defined below, and $R^5$ is lower alkyl.

It is also reported that as shown in the diagram, a keto-form β-lactam compound is enolized into an enol ether or vinyl halide, followed by halogenation with N-bromosuccinimide (NBS) or N-chlorosuccinimide (NCS) in the presence of a radical generating agent (JP-A- 135859/1983). Since this process requires use of a hazardous reagent for reaction, processes which are industrially more feasible are desired.

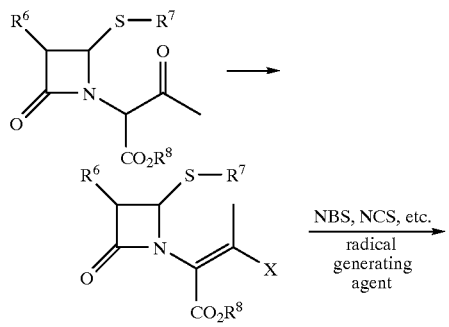

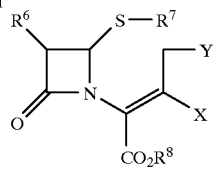

wherein $R^6$ is phthalimido, aryloxyalkaneamido or alkanoyl, $R^7$ is thiocyanato, alkanoyl, arylthio, benzothiazolethio, or alkoxycarbonyl which may be substituted with alkoxyl, cycloalkyl or the like, $R^8$ is alkyl which may be substituted with a halogen, aryl or the like, X is chlorine or the like, and Y is a halogen atom.

Further a process is already known for preparing the exo-methylenepenam compound of the invention which is represented by the general formula (5), by the decarboxylation Pummerer-type transition reaction of penam-2-carboxylic acid derived from penicillin as illustrated in Diagram (A) (Bawldwin et al., J. Chem. Soc., Chem. Commun., 1987, 81), whereas this process comprises as many as eight reaction steps, and is as low as up to 6% in overall yield and by no means feasible.

Diagram (A)

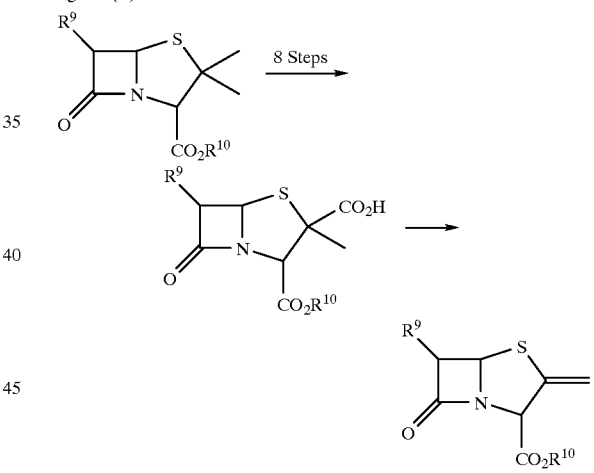

Also known are a synthesis process wherein an allenyl β-lactam compound obtained from penicillin is subjected to acid hydrolysis, followed by intramolecular cyclization (S. Torii et al., Tetrahedron Lett., 1991, 32, 7445) as shown in Diagram (B), and a synthesis process wherein an allenyl β-lactam compound is subjected to a reductive cyclization reaction (S. Torii et al., Synlett., 1992, 878, S. Torii et al., Chemistry Express, 1992, 7, 885, J. Chem. Soc., Chem. Commun., 1992, 1793). These processes nevertheless have various problems such as cumbersomeness of the reaction procedure for industrial operation since the reaction is conducted via an unstable allene compound as an intermediate.

Diagram (B)

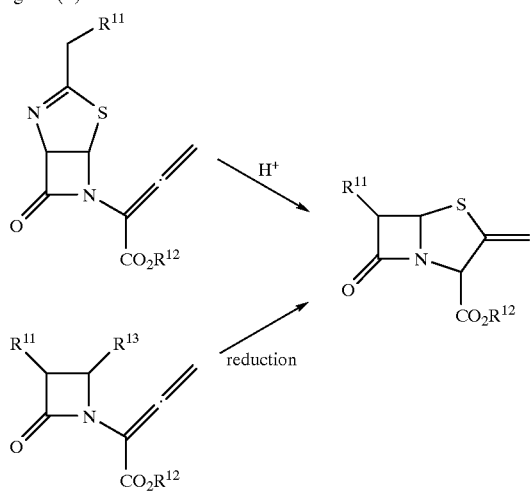

An object of the present invention is to provide a process adapted to produce a β-lactam halide compound represented by the general formula (2) from a β-lactam halide compound represented by the general formula (1) and readily available industrially, in a high yield with a high purity through a safe and simplified procedure, the process being developed by realizing milder conditions for effecting halogenation and a reaction for introducing the leaving group.

Another object of the invention is to provide a process adapted to produce an exo-methylenepenam compound of the general formula (5) from the β-lactam halide compound of the general formula (2) in a high yield with a high purity through a safe and simplified procedure by developing a novel metal reduction system and a novel electrolytic reduction system and thereby effecting allenization and conversion to an exo-methylenepenam at the same time efficiently.

DISCLOSURE OF THE INVENTION

The present invention relates to a process for producing a β-lactam halide compound represented by the general formula (2) which process is characterized in that the hydroxyl group of a β-lactam halide compound represented by the general formula (1) is substituted with a halogen atom or a leaving group

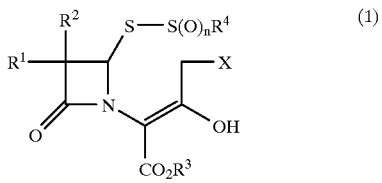

wherein $R^1$ is a hydrogen atom, amino or protected amino, $R^2$ is a hydrogen atom, halogen atom, lower alkoxyl, lower acyl, or lower alkyl having hydroxyl or protected hydroxyl as a substituent, $R^3$ is a hydrogen atom or carboxylic acid protective group, $R^4$ is aryl or aryl having a substituent, X is a halogen atom, and n is 0 to 2

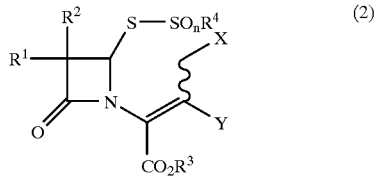

wherein $R^1$, $R^2$, $R^3$, $R^4$, X and n are as defined above, and Y is a halogen atom or a leaving group.

The present invention further provides a process for preparing an exo-methylenepenam compound represented by the general formula (5) characterized in that a β-lactam halide compound represented by the general formula (2) is reduced with a metal having a standard oxidation-reduction potential of up to −0.3 (V/SCE) in an amount of at least one mole per mole of the halide compound and with a metal compound having a higher standard oxidation reduction potential than the metal in an amount of 0.0001 to 10 moles per mole of the halide compound, or is subjected to an electrolytic reduction process to obtain the exo-methylenepenam compound

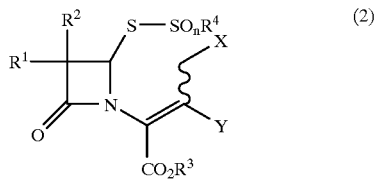

wherein $R^1$ is a hydrogen atom, amino or protected amino, $R^2$ is a hydrogen atom, halogen atom, lower alkoxyl, lower acyl, or lower alkyl having hydroxyl or protected hydroxyl as a substituent, $R^3$ is a hydrogen atom or carboxylic acid protective group, $R^4$ is aryl or aryl having a substituent, X is a halogen atom, Y is a halogen atom or a leaving group and n is 0 to 2

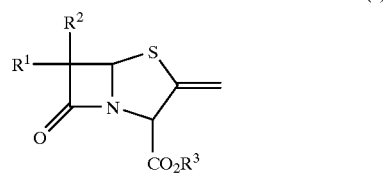

wherein $R^1$, $R^2$ and $R^3$ are as defined above.

Examples of groups mentioned herein are as follows.

Exemplary of the protected amino represented by $R^1$ are amido groups such as phenoxyacetamido, p-methylphenoxyacetamido, p-methoxyphenoxyacetamido, p-chlorophenoxyacetamido, p-bromophenoxyacetamido, phenylacetamido, p-methylphenylacetamido, p-methoxyphenylacetamido, p-chlorophenylacetamido, p-bromophenylacetamido, phenylmonochloroacetamido, phenyldichloroacetamido, phenylhydroxyacetamido, thienylacetamido, phenylacetoxyacetamido, α-oxophenylacetamido, benzamido, p-methylbenzamido, p-methoxybenzamido, p-chlorobenzamido, p-bromobenzamido, phenylglycylamido, phenylglycylamido having protected amino, p-hydroxyphenylglycylamido, p-hydroxyphenylglycylamido having protected amino and/or protected hydroxyl, etc.; imido groups such as phthalimido, nitrophthalimido, etc., in addition to the groups disclosed in Theodora W. Greene, 1981, "Protective Groups in Organic Synthesis" (hereinafter referred to merely as the "literature"), Chap. 7 (pp. 218~287). Examples of protective groups for the amino of phenylglycylamido group and p-hydroxyphenylglycylamido group are those disclosed in the literature, Chap. 7 (pp. 218~287). Examples of protective groups for the hydroxyl of p-hydroxyphenylglycylamido group are those disclosed in the literature, Chap.2 (pp. 10~72).

Examples of halogen atom represented by $R^2$ are fluorine, chlorine, bromine or iodine atom. Exemplary of the lower alkoxyl represented by $R^2$ are straight-chain or branched $C_{1-4}$ alkoxyl groups such as methoxy, ethoxy, n-propoxy, isopropoxy, n-butoxy, isobutoxy, sec-butoxy and tert-butoxy groups.

Exemplary of the lower acyl represented by $R^2$ are straight-chain or branched $C_{1-4}$ acyl groups such as formyl, acetyl, propionyl, butyryl and isobutyryl.

Examples of protective groups for the protected hydroxyl in the lower alkyl represented by $R^2$ and substituted with hydroxyl or protected hydroxyl, and for the protected hydroxyl represented by $R^2$ are those disclosed in the literature, Chap. 2 (pp. 10~72). The substituted lower alkyl represented by $R^2$ may have as its substituent(s) one or at least two same or different groups selected from among hydroxyl and the protected hydroxyl groups. Such substituent(s) may be positioned on at least one carbon atom of the alkyl. Examples of lower alkyl are straight-chain or branched $C_{1-4}$ alkyl group such as methyl, ethyl, n-propyl, isopropyl, n-butyl, isobutyl, sec-butyl or tert-butyl.

Exemplary of the carboxylic acid protecting group represented by $R^3$ are allyl, benzyl, pmethoxybenzyl, p-nitrobenzyl, diphenylmethyl, trichloromethyl, tert-butyl, and those disclosed in the literature, Chap. 5 (pp. 152~192).

Examples of aryl and substituted aryl represented by $R^4$ are phenyl, naphthyl, nitrogen-containing heterocyclic group, etc. Exemplary of the nitrogen-containing heterocyclic groups are benzothiazol group, triazol group, thiazol group, tetrazol group, etc. Exemplary of the substituent which may be substituted in the aryl are halogen atoms (such as fluorine, chlorine, bromine, iodine atom), straight-chain or branched $C_{1-4}$ alkoxyl groups (such as methoxy, ethoxy), straight-chain or branched $C_{1-4}$ alkylthio groups (such as methythio, ethylthio), straight-chain or branched $C_{1-4}$ alkylsulfonyloxy groups (such as methanesulfonyloxy, trifluoromethanesulfonyl-oxy), aromatic sulfonyloxy or substituted aromatic sulfonyloxy (such as benzenesulfonyloxy, toluenesulfonyloxy), straight-chain or branched $C_{1-4}$ alkyl groups (such as methyl, ethyl), amino, amino which has as a substituent one or two straight-chain or branched $C_{1-4}$ alkyl groups (such as methylamino, dimethylamino, ethylamino, diethylamino), hydroxyl, acyloxy group represented by R'COO— wherein R' is phenyl, tolyl, or straight-chain or branched $C_{1-4}$ alkyl group (such as phenylcarbonyloxy, acetyloxy), acyl group represented by R'CO—wherein R' is as defined above (such as phenylcarbonyl, acetyl), nitro, cyano, phenyl, etc. When the aryl represented by Ar is phenyl group, the aryl may have 1 to 5, especially 1, 2 or 3, same or different groups selected from among the above substituents. When the aryl represented by Ar is naphtyl group, the aryl may have 1 to 7, especially 1, 2 or 3, same or different groups selected from among the above substituents.

Examples of halogen atoms represented by X, Y are fluorine, chlorine, bromine or iodine atom. Exemplary of the leaving groups represented by Y are lower alkylsulfonyloxy or substituted lower alkylsulfonyloxy (such as methanesulfonyloxy, trifluoromethanesulfonyloxy, trichloromethanesulfonyloxy), aromatic sulfonyloxy or substituted aromatic sulfonyloxy (such as benzenesulfonyloxy, toluenesulfonyloxy), halogenated sulfonyloxy or substituted halogenated sulfonyloxy (such as fluoromethanesulfonyloxy), lower alkylphosphoryloxy or substituted lower alkylphosphoryloxy (such as trimethylphosphonyloxy, triethylphosphonloxy, tributylphosphoryloxy), aromatic phosphoryloxy or substituted aromatic phosphoryloxy (such as triphenylphosphoryloxy, tritolylphosphoryloxy), etc.

The β-lactam compound represented by the general formula (1) for use as a starting material of the present invention can be prepared, for example, from a β-lactam halide compound represented by the general formula (4) by a process disclosed in literature (S. Torii et al., Chemistry Letter, 1990, 1867), or by reacting this compound with ozone in an inert solvent

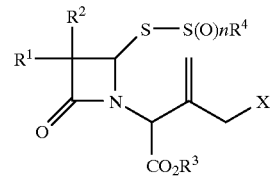

(4)

wherein $R^1$, $R^2$, $R^3$, $R^4$ and X are as defined above.

The β-lactam halide compound of the general formula (1) obtained can be purified in a usual manner for isolation but is usable as prepared for the next reaction.

A halogenating agent or agent for generating a leaving group is then caused to act on the hydroxyl group of the β-lactam halide compound of the general formula (1) thus obtained, whereby the compound (1) can be converted to a β-lactam halide compound represented by the general formula (2). Alternatively, the compound (1) is acted on with the leaving group generating agent first and then with the halogenating agent, whereby the β-lactam halide compound (2) can be prepared under milder conditions.

Examples of useful halogenating agents are phosphorus(V) chlorides such as phosphorus oxychloride and pentachloride, phosphorus(III) chlorides and bromides such as phosphorus trichloride and phosphorus tribromide, triarylphosphine-halogen complexes such as triarylphosphine-dichlorine complex and triarylphosphine-dibromine complex which may have a substituent, mixtures of a triarylphosphine or trialkylphosphine which may have a substituent and a halogen molecule, thionyl halides such as thionyl chloride and thionyl bromide, sulfonyl halides such as sulfonyl chloride and sulfonyl bromide, etc. Usual halogenating agents for the hydroxyl group are usable without any particular limitations. These halogenating agents are used usually in an amount of about 1 to about 50 moles, preferably about 1 to about 10 moles, per mole of the compound of the general formula (1). The halogenating agent can be used in combination with an inorganic base such as sodium bicarbonate or sodium carbonate, organic base such as triethylamine, ethyldiisopropylamine or N,N-dimethylaniline, or basic resin such as Amberlite XE-583. While the above halogenating agents are usable as the halogenating agent to be used subsequently to the leaving group generating agent used first, other examples of such agents usable for the subsequent reaction include alkali metal halide salts such as lithium chloride and lithium bromide, alkaline-earth metal halide salts such as calcium chloride and calcium bromide, and aluminum halide salts such as aluminum chloride and aluminum bromide. These halogen salts are used usually in an amount of about 1 to about 50 moles, preferably about 1 to about 10 moles, per mole of the compound of the general formula (1). The halogen salts are usable singly or in combination of at least two of them.

Examples of leaving group generating agents usable are methanesulfonyl chloride, trifluoromethanesulfonyl chloride and like lower alkylsulfonyl chlorides which may have a substituent, benzenesulfonyl chloride, toluenesulfonyl chloride and like aromatic sulfonic acid chlorides which may have a substituent, methanesulfonic anhydride, trifluoromethanesulfonic anhydride and like lower alkylsulfonic anhydrides which may have a substituent, benzenesulfonic anhydride, toluenesulfonic acid anhydride and like aromatic sulfonic anhydrides which may have a substituent, diethylphosphoryl chloride and like lower alkylphosphoryl chlorides which may have a substituent, diphenylphosphoryl chloride and like aromatic phosphoryl chlorides which may have a substituent, etc. These agents are used usually in an amount of about 1 to about 50 moles, preferably about 1 to about 10 moles, per mole of the compound of the general formula (1). The leaving group generating agent can be used in combination with, for example, an inorganic base such as sodium bicarbonate or sodium carbonate, organic base such as triethylamine, ethyldiisopropylamine or N,N-dimethylaniline, or basic resin such as Amberlite XE-583. Examples of substituents which may be present in these lower alkylsulfonyl chlorides, lower alkylsulfonyl anhydrides and lower alkyl phosphoryl chlorides are halogen atoms (such as fluorine, chlorine, bromine and iodine atoms), straight-chain or branched $C_{1\sim4}$ alkoxyl groups (such as methoxy, ethoxy), straight-chain or branched $C_{1\sim4}$ alkylthio groups (such as methylthio, ethylthio), straight-chain or branched $C_{1\sim4}$ alkylsulfonyloxy groups (such as methanesulfonyloxy, trifluoromethanesulfonyloxy), straight-chain or branched $C_{1\sim4}$ alkyl groups (such as methyl, ethyl), amino, amino which has as a substituent one or two straight-chain or branched $C_{1\sim4}$ alkyl groups (such as methylamino, dimethylamino, ethylamino, diethylamino), acyloxy group represented by R'COO— wherein R' is phenyl, tolyl, or straight-chain or branched $C_{1\sim4}$ alkyl group (such as phenylcarbonyloxy, acetyloxy), acyl group represented by R'CO— wherein R' is as defined above (such as phenylcarbonyl, acetyl), nitro, cyano, phenyl, etc. The lower alkylsulfonyl chlorides or anhydrides or lower alkylphosphoryl chlorides may have 1 to 5, preferably 1 to 3, such substituents which are different or of the same kind. Examples of substituents which may be present in the aromatic sulfonyl chlorides, aromatic sulfonyl anhydrides and aromatic phosphoryl chlorides are the same as those exemplified for the lower alkylksulfonyl chlorides or anhydrides or lower alkylphosphoryl chlorides. In the case where the aromatic group is phenyl, 1 to 5, preferably 1, 2 or 3, such substituents may be present, or when the aromatic group is naphthyl, 1 to 7, preferably 1 to 3, such substituents may be present. These substituents are different or of the same kind.

Examples of solvents useful in the above reaction are lower alkyl esters of lower carboxylic acids such as methyl formate, ethyl formate, propyl formate, butyl formate, methyl acetate, ethyl acetate, propyl acetate, butyl acetate, methyl propionate and ethyl propionate, ketones such as acetone, methyl ethyl ketone, methyl propyl ketone, methyl butyl ketone, methyl isobutyl ketone and diethyl ketone, ethers such as diethyl ether, ethyl propyl ether, ethyl butyl ether, dipropyl ether, diisopropyl ether, dibutyl ether, methyl cellosolve and dimethoxyethane, cyclic ethers such as tetrahydrofuran, dioxane and dioxolan, nitriles such as acetonitrile, propionitrile, butyronitrile, isobutyronitrile and valeronitrile, substituted or unsubstituted aromatic hydrocarbons such as benzene, toluene, xylene, chlorobenzene and anisole, hydrocarbon halides such as dichloromethane, chloroform, dichloroethane, trichloroethane, dibromoethane, propylene dichloride, carbon tetrachloride and Freons, aliphatic hydrocarbons such as pentane, hexane, heptane and octane, cycloalkanes such as cyclopentane, cyclohexane, cycloheptane and cyclooctane, amides such as dimethylformamide and dimethylacetamide, dimethylsulfoxide, etc. These solvents are used singly or in admixture of at least two of them. These solvents are used in an amount of about 10 to about 200 liters, preferably about 20 to about 100 liters, per kilogram of the compound of the formula (1). The reaction is conducted usually at $-80°$ C. to $80°$ C., preferably $-70°$ C. to $50°$ C. The reaction can be conducted, as required, in a sealed vessel, or at an atmosphere of an inert gas such as nitrogen gas. The resulting halogenated β-lactam compound of the formula (2) can be isolated by the usual purification method.

The structure of geometric isomer of the α-position substituent is likely to alter during the present reaction or subsequent purification step to undergo cis-trans isomerization. This case is to be included also within the scope of the invention.

The β-lactam halide compound of the invention represented by the general formula (2) and prepared by the foregoing process can alternatively be prepared, for example, by the following process. The desired product can be obtained by reacting a β-lactam compound represented by the general formula (6) and known in literature (S. Tori et al., Chemistry Lett., 1990, 1867) with sulfonyl anhydride or a sulfonyl halide which may have a substituent and an organic base, or with a phosphorus halide compound in an inert solvent

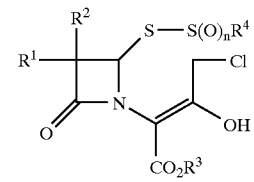

(6)

wherein $R^1$, $R^2$, $R^3$, $R^4$ and n are as defined above.

The reaction is conducted in a suitable solvent. Examples of solvents useful in the reaction are lower alkyl esters of lower carboxylic acids such as methyl formate, ethyl formate, propyl formate, butyl formate, methyl acetate, ethyl acetate, propyl acetate, butyl acetate, methyl propionate and ethyl propionate, ketones such as acetone, methyl ethyl ketone, methyl propyl ketone, methyl butyl ketone, methyl isobutyl ketone and diethyl ketone, ethers such as diethyl ether, ethyl propyl ether, ethyl butyl ether, dipropyl ether, diisopropyl ether, dibutyl ether, methyl cellosolve and dimethoxyethane, cyclic ethers such as tetrahydrofuran, dioxane and dioxolan, nitriles such as acetonitrile, propionitrile, butyronitrile, isobutyronitrile and valeronitrile, substituted or unsubstituted aromatic hydrocarbons such as benzene, toluene, xylene, chlorobenzene and anisole, hydrocarbon halides such as dichloromethane, chloroform, dichloroethane, trichloroethane, dibromoethane, propylene dichloride, carbon tetrachloride and Freons, aliphatic hydrocarbons such as pentane, hexane, heptane and octane, cycloalkanes such as cyclopentane, cyclohexane, cycloheptane and cyclooctane, amides such as dimethylformamide and dimethylacetamide, cyclic amides such as N-methylpyrrolidinone, dimethylsulfoxide, etc. These solvents are used singly or in admixture of at least two of them. These solvents may contain water as required. These solvents are used in an amount of about 10 to about 200 liters, preferably about 20 to about 100 liters, per kilogram of the compound of the formula (6). The reaction is conducted usually at −78° C. to 60° C., preferably −40° C. to 30° C. Examples of useful bases are N,N,N-tri lower alkyl amines such as trimethylamine, dimethylethylamine, triethylamine and diisopropylethylamine, N-lower alkyl azacycloalkanes such as N-methylpiperidine and N-ethylpiperidine, N-lower alkyl azaoxycycloalkanes such as N-methylmorpholine and N-ethylmorpholine, N-phenyl lower alkyl-N,N-di lower alkyl amines such as N-benzyl-N,N-dimethylamine and N-benzyl-N,N-diethylamine, N,N-dialkyl aromatic amines such as N,N-dimethylaniline, nitrogen-containing aromatic amines such as pyridine, bicycloamines such as diazabicycloundecene and diazabicyclononene, and a mixture of these amines. These bases are used usually in an amount of 1 to 10 equivalents based on the β-lactam compound of the formula (6). When required, it is recommended the base is added until the β-lactam compound of the formula (6) is consumed. The resulting halogenated β-lactam compound of the formula (2) can be isolated by the usual purification method but can be used in the next reaction without purification.

The β-lactam halide compound represented by the general formula (2) can be converted to an exo- methylenepenam compound represented by the general formula (5) by reacting the halogen atom of the compound (2) with a metal having a standard oxidation-reduction potential of up to −0.3 (V/SCE) in an amount of at least one mole per mole of the compound (2) and a metal compound having a higher standard oxidation-reduction potential than the metal in an amount of 0.0001 to 10 moles per mole of the compound (2), or by subjecting the compound (2) to an electrolytic reduction process in an organic solvent. It is thought that the above reaction of the invention first forms an allene intermediate as shown below, followed by the reduction of the group S—SOnR⁴ to give an exo-methylenepenam derivative.

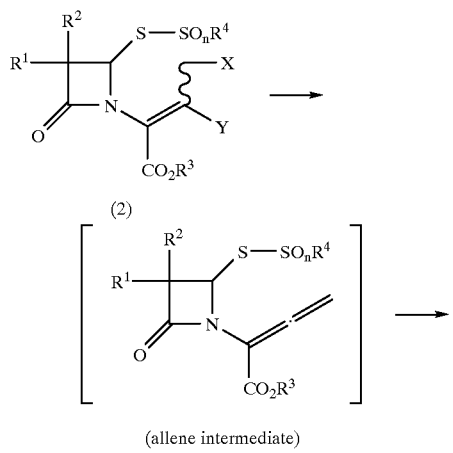

(allene intermediate)

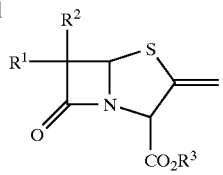

(5)

Examples of metals having a standard oxidation-reduction potential of up to −0.3 (V/SC) are magnesium, aluminum, zinc, iron, nickel, tin, lead, etc., among which magnesium, aluminum, zinc and tin are desirable to use. The shape of these metals is not limited particularly but can be any of a wide variety of forms such as powder, plate, foil, lump and wire. Preferably, the metal to be used is in the form of a powder or foil. The particle size of the powdery metal is preferably about 100 to about 300 mesh although variable over a wide range. These metals are used usually in an amount of about 1 to about 50 moles, preferably about 1 to about 10 moles, per mole of the compound of the general formula (2).

Examples of metal compounds having a higher standard oxidation-reduction potential than the above metals are lead compounds (such as lead fluoride, lead chloride, lead bromide, lead iodide and like lead halides, lead nitrate, lead sulfate, lead perchlorate, lead borate, lead carbonate, lead phosphate and like inorganic salts of lead, lead acetate, lead oxalate, lead stearate and like fatty acid salts of lead, lead oxide and lead hydroxide), copper compounds (such as copper fluoride, copper chloride, copper bromide, copper iodide and like copper halides, copper nitrate, copper sulfate, copper perchlorate, copper borate, copper carbonate, copper phosphate and like inorganic salts of copper, and copper oxalate), titanium compounds (such as titanium fluoride, titanium chloride, titanium bromide, titanium iodide and like titanium halides, and titanium nitrate, titanium sulfate and like inorganic salts of titanium), bismuth compounds (such as bismuth fluoride, bismuth chloride, bismuth bromide, bismuth iodide and like bismuth halide, bismuth nitrate, bismuth sulfate and like inorganic salts of bismuth), antimony compounds (such as antimony fluoride, antimony chloride, antimony bromide, antimony iodide and like antimony halides, antimony sulfate and like inorganic salts of antimony, and antimony oxide), and nickel compounds (such as nickel fluoride, nickel chloride, nickel bromide, nickel iodide and like nickel halides, nickel nitrate, nickel sulfate, nickel perchlorate, nickel borate, nickel carbonate, nickel phosphate and like inorganic salts of nickel, nickel acetate and like fatty acid salts of nickel, tetrachloronickel (II) tetraethylammonium, tetrabromonickel(II) tetraethylammonium, hexamminenickel(II), tris(ethylenediamine)nickel(II) sulfate, ethylenediaminetetraaquanickel(II) sulfate monohydrate, dinitrobis(ethylenediamine)nickel(II) perchlorate, bis perchlorate(N,N-dimethylethylenediamine)nickel(II) perchlorate and like inorganic complexes of nickel, dichloro(bipyridyl)nickel(II), chloro(n-cyclopentadienyl)(triphenylphosphine)nickel(II), dibromobis(triphenylphosphine)nickel(II), dichlorobis{1,1'-(diphenylphosphino)ferrocene}nickel(II) and like organic complexes of nickel(II), and tetrakis(triphenylphosphine)nickel(0), tris(triphenylphosphine)nickel(0), nickel(0) acetylacetonato, nickel (0)hexafluoroacetylacetonato and like organic complexes of nickel(0)). These metal compounds may be used singly or as a mixture of at least two of them. These metal compounds are used usually in an amount of 0.0001 to 30 moles, preferably 0.001 to 10 moles, per mole of the compound of the general formula (2).

Examples of combinations of metals up to −0.3 (V/SCE) in standard oxidation-reduction potential and metal compounds having a higher standard oxidation-reduction potential are Al/Pb compound, Al/Bi compound, Zn/Pb compound, Zn/Bi compound, Mg/Bi compound, Mg/Cu compound, Sn/Ti compound, Sn/Bi compound, Sn/Sb compound, etc., among which the combinations of Al/Pb compound and Zn/Bi compound are preferred.

Examples of useful solvents for the present reaction are the same as those for use in the reaction for preparing the compound of the general formula (2) from the compound of the general formula (6). These solvents are usable also as rendered hydrous. These solvents are used usually in an amount of about 10 to about 200 liters, preferably about 20 to about 100 liters, per kg of the compound of the general formula (2). The reaction is conducted at a temperature usually of −10 to 80° C., preferably of 0 to 50° C. The reaction of the invention proceeds satisfactorily even around room temperature. Further when required, the reaction can be conducted within a closed container or in an insert solvent such as nitrogen gas. The exo- methylenepenam derivative of the formula (5) obtained can be isolated by a usual purification procedure.

According to the present invention, the desired exomethylenepenam derivative of the general formula (5) can be prepared also by electrolytically reducing the compound (2) in an organic solvent. The organic solvent for use in the electroreduction reaction of the invention can be any of the solvents useful for the foregoing reduction reaction. In carrying out the electroreduction reaction of the present invention, a supporting electrolyte is added to the reaction system. Examples of useful supporting electrolytes are metal perchlorate salts such as lithium perchlorate, sodium perchlorate and magnesium perchlorate, ammonium perchlorate salts such as ammonium perchlorate, tetraethylammonium perchlorate and tetrabutylammonium perchlorate, ammonium halide salts such as ammonium chloride, ammonium bromide, ammonium iodide, tetraethylammonium chloride and tetrabutylammonium bromide, metal tetrafluroborate salts such as lithium tetrafluroborate and sodium tetraflurobate, ammonium tetrafluroborate salts such as tetraethylammonium tetrafluroborate and tetrabutylammonium tetrafluroborate, amines such as triethylamine, collidine, lutidine, pyridine, piperidine, N-methylmorpholine, 1,5-diazabicyclo[3,4,0]nonene-5 (DBN) and 1,5-diazabicyclo[5,4,0]undecene-5 (DBU), carboxylic acids such as acetic acid, monochloroacetic acid and trifluoroacetic acid, etc. These support electrolytes are used singly or in the form of a mixture of at least two of them. Preferable to use are the carboxylic acids. The support electrolyte is used usually in an amount of about 0.1 to about 100 wt. %, preferably about 0.1 to about 50 wt. %, based on the solvent.

A wide variety of electrodes useful for usual electrolytic reactions are usable for the electrolytic reduction process of the present invention. For example, platinum, tin, aluminum, stainless steel, nickel, lead oxide, carbon, iron oxide, titanium, etc. are usable as materials for the positive electrode, and platinum, tin, aluminum, stainless steel, zinc, lead, copper, carbon, etc. as materials for the negative electrode. It is preferable to use tin, zinc, lead and copper for the negative electrode.

It is likely that the electroreduction of the invention will be effected with an improved current efficiency by adding to the electrolytic system a metal halide, inorganic acid salt, organic acid salt or oxide having an oxidation reduction potential not higher than that of the negative electrode material used. Examples of such additives usable are halides of metals such as tin, zinc, lead, bismuth and titanium (e.g., fluorides, chlorides, bromides and iodides), inorganic acid salts (such as nitrates, sulfates, perchlorates, borates, phosphates and carbonates), organic acid salts (such as oxalates, stearates and acetates), oxides, etc. These additives can be used singly or in the form of a mixture of at least two of them. Such additives are used in an amount of about 0.1 to about 1 mole per mole of the compound of the general formula (2). If the additive is used, the supporting electrolyte need not always be used as the case may be.

The electroreduction of the present invention is characterized in that this process can be practiced within a single cell without a need to separate the positive electrode from the negative electrode although the electrodes can be separated by a partition membrane. The reaction temperature is usually in the range of −10° C. to 50° C.

The present reaction can be carried out either at a constant current or at a constant voltage. However, it is desirable to use the constant-current electrolysis process in view of the simplicity of the device and procedure. While the electrolysis can be effected with direct current or alternating current, it is also possible to conduct the reaction by changing the direction of current every second or every 30 seconds. The current density is usually 1 to 500 mA/cm$^2$, preferably 1 to 50 mA/cm$^2$. The quantity of electricity to be used is usually 2 to 10 F/mole, preferably 2 to 5 F/mole although the quantity varies with the shape of the electrolytic cell, the kind of compound (2) and the kind of solvent used and can not therefore be determined specifically. The reaction is completed by passing the above-mentioned quantity of electricity.

The exo-methylenepenam derivative of the formula (5) obtained can be isolated by a usual purification procedure.

BEST MODE OF CARRYING OUT THE INVENTION

The present invention will be described below in detail with reference to examples, wherein Ph stands for $C_6H_5$—, Et for ethyl, Bu for butyl and bby for bipyridyl.

EXAMPLE 1

A 100 mg quantity of compound (1a) ($R^1$=PhCH$_2$CONH, $R^2$=H, $R^3$=CH$_2$C$_6$H$_4$OCH$_3$-p, $R^4$=Ph, X=Cl) was weighed out, placed into a 10-ml egg-plant type flask and dissolved in 11 18 Nl of N,N-dimethylformamide. To the solution was added a solution of 18 Nl of phosphorus oxychloride in 1 ml of N,N-dimethylformamide, followed by stirring at room temperature for 1 hour. The reaction mixture was poured into water and extracted with ethyl acetate. The extract was washed with water twice and then with brine once and thereafter dried over anhydrous sodium sulfate. The resulting extract was concentrated in vacuo to remove the solvent, and the residue was subsequently purified by silica gel column chromatography to afford compound 2a (Y=Cl) (95 mg, 92%). $^1$H—NMR (CDCl$_3$)δ:3.64(d, J=16.8 Hz, 1H), 3.71(d, J=16.8 Hz, 1H), 3.81(s, 3H), 4.27(d, J=12.2 Hz, 1H), 4.70(d, J=12.2 Hz, 1H), 4.73(dd, J=5.6, 6.4 Hz, 1H), 5.09(d, J=11.8 Hz, 1H), 5.20(d, J=11.8 Hz, 1H), 5.87(d, J=5.6 Hz, 1H), 5.97(d, J=6.4 Hz, 1H), 6.87~7.74(m, 14H).

EXAMPLES 2 to 7

The same reaction as in Example 1 was performed using the following halogenating agents.

| Example | halogenating agent | yield (%) |
| --- | --- | --- |
| 2 | (COCl)$_2$ | 90 |
| 3 | SOCl$_2$ | 86 |
| 4 | PCl$_3$ | 89 |
| 5 | PCl$_5$ | 83 |
| 6 | S$_2$Cl$_2$ | 78 |
| 7 | Vilsmeyer reagent | 91 |

EXAMPLES 8 to 15

The same reaction as in Example 1 was performed using Vilsmeyer reagent and the following solvents.

| Example | solvent | yield (%) |
| --- | --- | --- |
| 8 | CH$_2$Cl$_2$ | 85 |
| 9 | CH$_2$ClCH$_2$Cl | 80 |
| 10 | CHCl$_3$ | 81 |
| 11 | THF | 78 |
| 12 | dioxane | 82 |
| 13 | dioxolan | 85 |
| 14 | DME | 76 |
| 15 | NMP | 89 |

EXAMPLE 16

A 200 mg quantity of compound (1a) ($R^1$=PhCH$_2$CONH, $R^2$=H, $R_3$=CH$_2$C$_6$H$_4$OCH$_3$-p, $R_4$=Ph, X=Cl), 73 mg of tosyl chloride and 81 mg of sodium carbonate were weighed out, placed into 10-ml egg-plant type flask and stirred at 3° C. for 2 hours along with 2 ml of N,N-dimethylformamide. The reaction mixture was poured into water and extracted with ethyl acetate. The extract was washed with water twice and then with brine once, and thereafter dried over anhydrous sodium sulfate. The resulting extract was concentrated in vacuo to remove the solvent, and the residue was subsequently purified by silica gel column chromatography, giving compound 2b (Y=OSO$_2$C$_6$H$_4$—CH$_3$-p) (236 mg, 95% ). $^1$H—NMR(CDCl$_3$)δ:2.38(s, 3H), 3.62(s, 2H), 3.90(s, 3H), 4.51(d, J=13.8 Hz, 1H), 4.82(d, J=13.8Hz, 1H), 5.27(s, 2H), 5.47(dd, J=4.7, 9.2 Hz, 1H), 5.91(d, J=4.7 Hz, 1H), 6.28(d, J=9.2 Hz, 1H), 6.96~7.91(m, 18H).

EXAMPLES 17 to 21

The same reaction as in Example 16 was preformed using the following solvents.

| Example | solvent | yield (%) |
| --- | --- | --- |
| 17 | NMP | 93 |
| 18 | THF | 86 |
| 19 | dioxane | 85 |
| 20 | dioxolan | 85 |
| 21 | CH$_2$Cl$_2$ | 72 |

EXAMPLE 22

A 200 mg quantity of compound (1a) ($R^1$=PhCH$_2$CONH, $R^2$=H, $R^3$=CH$_2$C$_6$H$_4$OCH$_3$-p, $R^4$=Ph, X=Cl) was weight out, placed into a 10-ml egg-plant type flask and cooled to −78° C. with addition of 2 ml of methylene chloride. To the cooled mixture were added 64 ml of trifluoromethanesulfonic acid anhydride and 106 ml of triethylamine, followed by stirring at the same temperature for 20 minutes. The reaction mixture was poured into 1N hydrochloric acid and extracted with methylene chloride. The extract was washed with water twice and then with brine once, and thereafter dried over anhydrous sodium sulfate. The resulting extract was concentrated in vacuo to remove the solvent, and the residue was purified by silica gel column chromatography, giving compound 2c (Y=OSO$_2$CF$_3$) (223 mg, 92%). $^1$H—NMR (CDCl$_3$)δ:3.62(d, J=19.2 Hz, 1H), 3.69 (d, J=19.2 Hz, 1H) , 3.79 (s, 3H), 4.31 (d, J=14.4 Hz, 1H), 4.74 (d, J=14.4 Hz, 1H), 4.83(dd, J=5.4, 6.9 Hz, 1H), 5.15(d, J=11.7 Hz, 1H), 5.23(d, J=11.7 Hz, 1H), 5.95(d, J=6.9 Hz, 1H), 6.00(d, J=5.4 Hz, 1H) , 6.88~7.78 (m, 14H)

EXAMPLE 23

Five gram of compound (2c) ($R^1$=PhCH$_2$CONH, $R^2$=H, $R^3$=CH$_2$C$_6$H$_4$OCH$_3$-p, $R^4$=Ph, X=Cl, Y=OSO$_2$CF$_3$) obtained in Example 22, 2.5 g of aluminum chloride and 2.8 g of lithium chloride were weighed out, placed into a 200-ml egg- plant type flask and stirred at room temperature for 4 hours and 20 minutes with addition of 125 ml of N-methylpyrrolidone. The reaction mixture was poured into water and extracted with ethyl acetate. The extract was washed with water twice and then with brine once, and thereafter dried over anhydrous sodium sulfate. The resulting extract was concentrated in vacuo to remove the solvent, and the residue was purified by silica gel column chromatography, affording compound 2a (Y=Cl) (3.87 g, 91%). The resulting compound was fully identical with that of Example 1 in $^1$H NMR.

Reference Example 1

A 100 mg quantity of compound (2a) of the invention was weighed out and dissolved in 2 ml of NMP. To the solution were added 300 mg of aluminum chloride and 100 mg of zinc, and the mixture was stirred at room temperature for 2 hours. The reaction mixture was poured into 1N hydrochloric acid and extracted with ethyl acetate. The extract was concentrated in vacuo, followed by silica gel column chromatography for purification, giving 3-chlorocephem (4). The compound 3-chlorocephem (4) can be converted by a process disclosed in literature to cefaclor which is widely used as an oral preparation. Stated more specifically, the compound (4) is deprotected at the 7- position with phosphorus pentachloride and pyridine (JP-A-3356/1986) and thereby converted to a compound (5), into which an amido side chain is introduced at the 7-position. Subsequently, the ester group at the 4-position is deprotected, giving cefaclor (JP-A-39313/1986). Given below is the reaction formula.

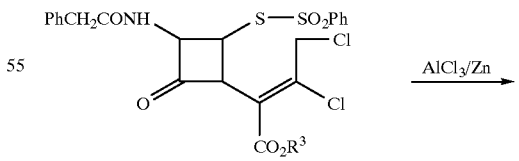

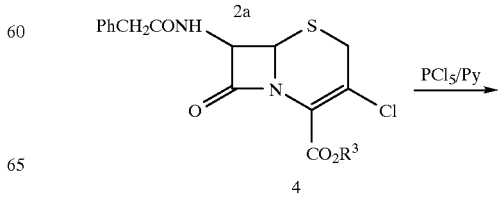

4

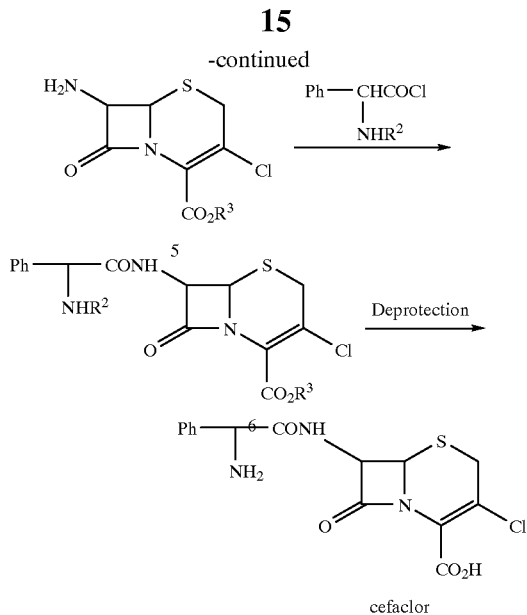

cefaclor

EXAMPLE 24

A 100 mg quantity of compound (2a) ($R^1$=PhCH$_2$CONH, $R^2$=H, $R^3$=CH$_2$C$_6$H$_4$OCH$_3$-p, $R^4$=Ph, X=Cl, Y=Cl), 100 mg of lead bromide and 100 mg of aluminum powder were weighed out, placed into a 10-ml egg-plant type flask and stirred at room temperature for 1 hour with addition of 2 ml of N,N-dimethylformamide. The reaction mixture was poured into 1N hydrochloric acid and extracted with ethyl acetate. The extract was washed with water twice and then with brine once, and thereafter dried over anhydrous sodium sulfate. The resulting extract was concentrated in vacuo to remove the solvent, and the residue was purified by silica gel column chromatography, giving compound 5a (67 mg, 99%).

$^1$H—NMR (CDCl$_3$)δ: 3.61(s, 2H), 5.25(m, 2H), 5.35(m, 1H), 5.59(d, J=4.0 Hz, 1H), 5.75(dd, J=4.0, 8.9 Hz, 1H), 6.12(d, J=8.9 Hz, 1H), 6.84(s, 1H), 7.22~7.40(m, 15H)

EXAMPLE 25

The same reaction as in Example 24 was conducted using,. as a starting material, compound (2d) ($R^1$= PhCH$_2$CONH, $R^2$=H, $R^3$=CHPh$_2$, $R^4$=Ph, X=Cl, Y=Cl) to obtain the compound 5b (68 mg, 97%).

$^1$H—NMR (CDCl$_3$)δ: 3.61(s, 2H), 3.80(s, 3H), 5.11(s, 2H), 5.18(dd, J=1.5, 1.7 Hz, 1H), 5.24(dd, J=1.5, 2.2 Hz, 1H), 5.35(dd, J=1.7, 2.2 Hz, 1H), 5.57(d, J=4.0 Hz, 1H), 5.75(dd, J=4.0, 9.3 Hz, 1H), 6.07(d, J=9.3 Hz, 1H), 6.85~7.40(m, 9H)

EXAMPLE 26

The same reaction as in Example 24 was conducted using, as a starting material, Compound (2e) ($R^1$=PhCH$_2$CONH, $R^2$=H, $R^3$=CH$_3$, $R^4$=Ph, X=Cl, Y=Cl) to obtain the compound 5c (60 mg, 98%)

$^1$H—NMR (CDCl$_3$)δ: 3.63(ABq,J=2.7 Hz, 2H), 3.78(s, 3H), 5.19(dd, J=1.9, 1.9 Hz, 1H), 5.28(dd, J=1.9, 1.9 Hz, 1H), 5.40(dd, J=1.9, 1.9 Hz, 1H), 5.60(d, J=4.0 Hz, 1H), 5.77(dd, J=4.0, 8.8 Hz, 1H), 6.20(d, J=8.8 Hz, 1H), 7.27~7.37(m, 5H)

EXAMPLE 27

The same reaction as in Example 24 was conducted using, as a starting material, Compound (2f) ($R^1$=H, $R^2$=H, $R^3$=CH$_2$C$_6$H$_4$OCH$_3$-p, $R^4$=Ph, X=Cl, Y=Cl) to obtain the compound 5d (54 mg, 90%).

$^1$H—NMR (CDCl$_3$)δ: 3.16(dd, J=1.5, 16.0 Hz, 2H), 3.66 (dd, J=4.0, 16.0 Hz, 1H), 3.82(s, 3H), 5.13(s, 2H), 5.24(dd, J=1.8, 1.8 Hz, 1H), 5.28(dd, J=1.8, 1.8 Hz, 1H), 5.32(dd, J=1.8, 1.8 Hz, 1H), 5.38(dd, J=1.5, 4.0 Hz, 1H), 6.87~7.30 (m, 4H)

EXAMPLE 28

The same reaction as in Example 24 was conducted using, as a starting material, Compound (2g) ($R^1$=H, $R^2$=H, $R^3$=CHPh$_2$, $R^4$=Ph, X=Cl, Y=Cl) to obtain the compound 5e (55 mg, 87%). $^1$H—NMR (CDCl$_3$)δ: 3.12(dd, J=1.5, 16.0 Hz, 2H), 3.60(dd, J=4.1, 16.0 Hz, 1H), 5.23(dd, J=1.8,1.8 Hz, 1H), 5.32(dd, J=1.8, 1.8 Hz, 1H), 5.36(dd, J=1.5, 4.1 Hz, 1H), 5.37(dd, J=1.8, 1.8 Hz, 1H), 6.87(s, 1H), 7.27~7.35(m, 10H).

EXAMPLE 29

The same reaction as in Example 24 was conducted using, as a starting material, Compound (2h) ($R^1$=PhCH$_2$CONH, $R^2$=H, $R^3$=CH$_2$C$_6$H$_4$OCH$_3$-p, $R^4$=Ph, X=Cl, Y=OSO$_2$CF$_3$) to obtain the compound 5a (49 mg, 86%). The resulting compound was fully identical with that of Example 24 in spectral data.

EXAMPLE 30

The same reaction as in Example 24 was conducted using, as a starting material, Compound (2i) ($R^1$=PhCH$_2$CONH, $R^2$=H, $R^3$=CHPh$_2$, $R^4$=Ph, X=Cl, Y=OSO$_2$CF$_3$) to obtain the compound 5b (51 mg, 85%). The resulting compound was fully identical with that of Example 25 in spectral data.

EXAMPLE 31

The same reaction as in Example 24 was conducted using, as a starting material, Compound (2j) ($R^1$=PhCH$_2$CONH, $R^2$=H, $R^3$=CH$_2$C$_6$H$_4$OCH$_3$-p, $R^4$=Ph, X=Cl, Y=OSO$_2$C$_6$H$_4$CH$_3$-p) to obtain the compound 5a (50 mg, 76%). The resulting compound was fully identical with that of Example 24 in spectral data.

EXAMPLE 32

The same reaction as in Example 24 was conducted using, as a starting material, Compound (2k) ($R^1$=PhCH$_2$CONH, $R^2$=H,. $R^3$=CHPh$_2$, $R^4$=Ph, X=Cl, Y=OSO$_2$C$_6$H$_4$CH$_3$-p) to obtain the compound 5b (52 mg, 72%). The resulting compound was fully identical with that of Example 25 in spectral data.

EXAMPLES 33 to 41

The same reaction as in Example 24 was performed using the following reducing agents.

| Example | metal compound | amount | metal | yield (%) |
|---|---|---|---|---|
| 33 | PbBr$_2$ | 0.1 eq. | Al | 92 |
| 34 | PbBr$_2$ | 1 eq. | Zn | 75 |
| 35 | PbCl$_2$ | 1 eq. | Al | 80 |
| 36 | Pb(OAc)$_2$ | 1 eq. | Al | 70 |
| 37 | BiCl$_3$ | 1 eq. | Al | 72 |
| 38 | BiCl$_3$ | 1 eq. | Zn | 83 |
| 39 | BiCl$_3$ | 1 eq. | Sn | 72 |

-continued

| Example | metal compound | amount | metal | yield (%) |
|---------|----------------|--------|-------|-----------|
| 40 | AlCl$_3$ | 1 eq. | Zn | 85 |
| 41 | AlCl$_3$ | 1 eq. | Mg | 71 |

EXAMPLES 42 to 47

The same reaction as in Example 24 was preformed using the following solvents.

| Example | solvent | yield (%) |
|---------|---------|-----------|
| 42 | NMP | 98 |
| 43 | DMA | 93 |
| 44 | HMPA | 82 |
| 45 | DMF/CH$_2$Cl$_2$ | 79 |
| 46 | DMF/CF$_3$COOH | 98 |
| 47 | NMP/CF$_2$COOH | 95 |

EXAMPLE 48

A 100 mg quantity of compound (2a) ($R^1$=PhCH$_2$CONH, $R^2$=H, $R^3$=CH$_2$C$_6$H$_4$OCH$_3$-p, $R^4$=Ph, X=Cl, Y=Cl), 11 mg of lead bromide and 50 mg of tetraethylammonium tosylate were weighed out, placed into a 20-ml branched test tube and stirred with addition of 10 ml of N,N-dimethylformamide to prepare a solution. Electricity was passed through the solution in an amount of 5 F/mole with a current of 7.5 mA (5 mA/cm$^2$) via a positive electrode of aluminum and a negative electrode of platinum provided in the solution. The reaction mixture was poured into 1N hydrochloric acid and extracted with ethyl acetate. The extract was washed with water twice and then with brine once, and thereafter dried over anhydrous sodium sulfate. The resulting extract was concentrated in vacuo to remove the solvent, and the residue was subsequently purified by silica gel column chromatography, giving compound 5a (54 mg, 80%).

EXAMPLES 49 to 59

The same reaction was performed using the following electrodes and the same other reaction conditions as above.

| Example | cathode | anode | yield (%) |
|---------|---------|-------|-----------|
| 49 | Al | C | 70 |
| 50 | Al | Al | 75 |
| 51 | Al | Pb | 72 |
| 52 | Al | Zn | 78 |
| 53 | Al | Sn | 76 |
| 54 | Sn | Pt | 69 |
| 55 | Sn | Pb | 74 |
| 56 | Sn | Sn | 72 |
| 57 | Zn | Pb | 75 |
| 58 | Zn | Zn | 70 |
| 59 | Pb | Pb | 76 |

EXAMPLES 60 to 67

The same reaction was performed using the following supporting electrolyte and the same other reaction conditions as above.

| Example | electrolyte | yield (%) |
|---------|-------------|-----------|
| 60 | Et$_4$NBr | 65 |
| 61 | Et$_4$NClO$_4$ | 73 |
| 62 | Bu$_4$NBr | 62 |
| 63 | LiClO$_4$ | 68 |
| 64 | H$_2$SO$_4$ | 70 |
| 65 | CH$_3$COOH | 73 |
| 66 | CH$_3$COOH | 70 |
| 67 | Bu$_4$NBF$_6$ | 62 |

EXAMPLES 68 to 74

The same reaction was performed using the following additives and the same other reaction conditions as above.

| Example | additive | yield (%) |
|---------|----------|-----------|
| 68 | PbCl$_2$ | 78 |
| 69 | PbI$_2$ | 75 |
| 70 | BiCl$_3$ | 72 |
| 71 | TiCl$_4$ | 74 |
| 72 | SbCl$_3$ | 68 |
| 73 | NiCl$_2$ (bpy) | 71 |
| 74 | ZrCl$_4$ | 62 |

EXAMPLES 75 to 80

The same reaction was performed using the following solvents and the same other reaction conditions as above.

| Example | additive | yield (%) |
|---------|----------|-----------|
| 75 | NMP | 95 |
| 76 | DMA | 90 |
| 77 | HMPA | 78 |
| 78 | DMF/CH$_3$COOH | 96 |
| 79 | DMF/CF$_3$COOH | 98 |
| 80 | NMP/CF$_3$COOH | 98 |

Reference Example 2

Bioorganic and Medicinal Chemistry Letters, 3, 2253 (1993) discloses a process for preparing a penem compound having β-lactamase inhibitory activity, for example, from exo-methylenepenam (5e) obtained by the present invention and serving as a starting material. This process generally comprises the following steps. An exo-methylenepenam compound (A) is decomposed by ozonolysis into a ketone (B), which is then reacted in the presence of trifluoromethanesulfonyl anhydride and a base to obtain an enol-triflate (C). This compound is reacted with various thiols (RSH) to derive a penem compound (D). The compound is deprotected and purified, affording a compound (E) having β-lactamase inhibitory activity.

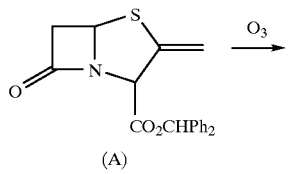

(A)

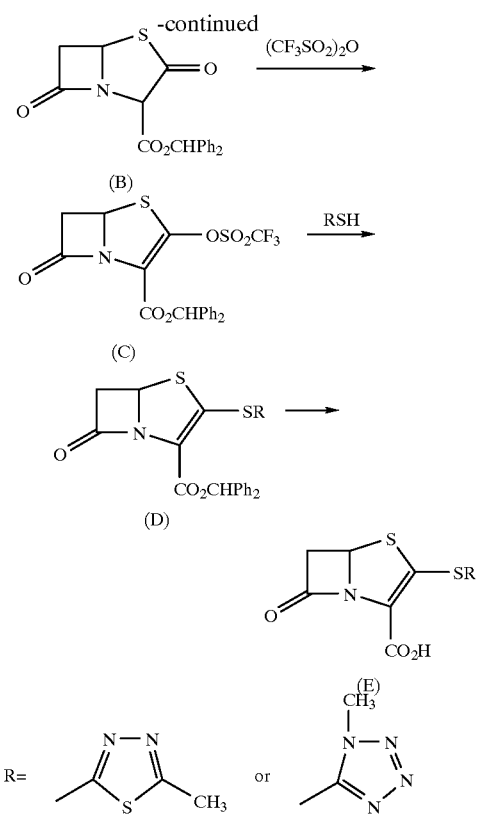

(Industrial Applicability)

According to the present invention, a β-lactam halide compound represented by the general formula (2) can be obtained-by a process using, as a starting material, β-lactam halide compound represented by the general formula (1) and readily available industrially, in a high yield with a high purity through a safe and simplified procedure, the process being developed by realizing milder conditions for effecting halogenation and a reaction for introducing the leaving group.

Further, an exo-methylenepenam compound of the general formula (5) can be obtained by a process using, as a starting material, the β-lactam halide compound of the general formula (2) in a high yield with a high purity through a safe and simplified procedure by developing a novel metal reduction system and a novel electroreduction system and thereby effecting allenization and conversion to an exo-methylenepenam at the same time efficiently.

We claim:

1. The process for producing a β-lactam halide compound of formula (2)

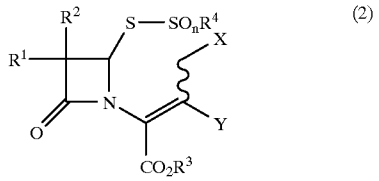

wherein $R^1$ is selected from the group consisting of hydrogen, amino and protected amino; $R^2$ is selected from the group consisting of hydrogen, halogen, $C_{1-4}$ alkoxy, formyl, acetyl, propionyl, butyryl, isobutyryl and $C_{1-4}$ alkyl which is substituted by hydroxyl or protected hydroxyl; $R^3$ is hydrogen or a carboxylic acid protecting group; $R^4$ is aryl or substituted aryl; X is halogen; n is 0 to 2; and Y is selected from the group consisting of a halogen atom, a substituted or unsubstituted lower alkylsulfonyloxy group, a substituted or unsubstituted aromatic sulfonyloxy group, a substituted or unsubstituted halogenated lower alky sulfonyloxy group, a substituted or unsubstituted lower alkylphosphoryloxy group and a substituted or unsubstituted aromatic phosphoryloxy group, the process comprising:

reacting a β-lactam halide compound of formula (1)

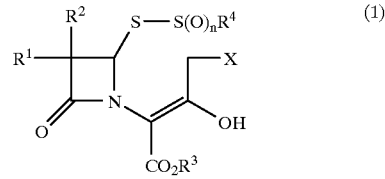

wherein $R^1$, $R^2$, $R^3$, $R^4$, X and n are as defined above, with an agent selected from the group consisting of (a) a halogenating agent, to obtain the compound of formula (2) wherein Y is a halogen atom;

(b) a reagent selected from the group consisting of (i) a substituted or unsubstituted lower alkylsulfonyl chloride, (ii) a substituted or unsubstituted aromatic sulfonic acid chloride, (iii) a substituted or unsubstituted lower alkylsulfonic anhydride, (iv) a substituted or unsubstituted aromatic sulfonic anhydride, (v) a substituted or unsubstituted lower alkylphosphoryl chloride and (vi) a substituted or unsubstituted aromatic phosphoryl chloride, to obtain the compound of formula (2) wherein Y is selected from the group consisting of a substituted or unsubstituted lower alkylsulfonyloxy group, a substituted or unsubstituted aromatic sulfonyloxy group, a substituted or unsubstituted halogenated lower alkyl sulfonyloxy group, a substituted or unsubstituted lower alkylphosphoryloxy group and a substituted or unsubstituted aromatic phosphoryloxy group; and (c) a reagent selected from the group consisting of (i) a substituted or unsubstituted lower alkylsulfonyl chloride, (ii) a substituted or unsubstituted aromatic sulfonic acid chloride, (iii) a substituted or unsubstituted lower alkylsulfonic anhydride, (iv) a substituted or unsubstituted aromatic sulfonic anhydride, (v) a substituted or unsubstituted lower alkylphosphoryl chloride and (vi) a substituted or unsubstituted aromatic phosphoryl chloride, and thereafter reacting the compound with a halogenating agent, to obtain the compound of formula (2) wherein Y is a halogen atom.

2. The process of claim 1, wherein the compound of formula (1) is reacted with a halogenating agent, to obtain the compound of formula (2) wherein Y is a halogen atom.

3. The process of claim 1, wherein the compound of formula (1) is reacted with a reagent selected from the group consisting of (i) a substituted or unsubstituted lower alkylsulfonyl chloride, (ii) a substituted or unsubstituted aromatic sulfonic acid chloride, (iii) a substituted or unsubstituted lower alkylsulfonic anhydride, (iv) a substituted or unsubstituted aromatic sulfonic anhydride, (v) a substituted or unsubstituted lower alkylphosphoryl chloride and (vi) a substituted or unsubstituted aromatic phosphoryl chloride, to obtain the compound of formula (2) wherein Y is selected from the group consisting of a substituted or unsubstituted lower alkylsulfonyloxy group, a substituted or unsubstituted aromatic sulfonyloxy group, a substituted or unsubstituted halogenated lower alkyl sulfonyloxy group, a substituted or unsubstituted lower alkylphosphoryloxy group and a substituted or unsubstituted aromatic phosphoryloxy group.

4. The process of claim 1, wherein the compound of formula (1) is reacted with a reagent selected from the group consisting of (i) a substituted or unsubstituted lower alkylsulfonyl chloride, (ii) a substituted or unsubstituted aromatic sulfonic acid chloride, (iii) a substituted or unsubstituted lower alkylsulfonic anhydride, (iv) a substituted or unsubstituted aromatic sulfonic anhydride, (v) a substituted or unsubstituted lower alkylphosphoryl chloride and (vi) a substituted or unsubstituted aromatic phosphoryl chloride, and thereafter reacting the compound with a halogenating agent, to obtain the compound of formula (2) wherein Y is a halogen atom.

5. The process of claim 1, wherein the halogenating agent in (a) is selected from the group consisting of a phosphorus (V) chloride, a phosphorus(lll) chloride, a phosphorus(lll) bromide, a triarylphosphine-halogen complex, a thionyl halide, a sulfonyl halide and a mixture of a triarylphosphine or trialkylphosphine and a halogen molecule.

6. The process of claim 1, wherein the halogenating agent in (c) is selected from the group consisting of a phosphorus (V) chloride, a phosphorus(lll) chloride, a phosphorus(lll) bromide, a triarylphosphine-halogen complex, a thionyl halide, a sulfonyl halide, an alkali metal halide salt, an alkaline-earth metal halide salt, an aluminum halide salt, and a mixture of a triarylphosphine or trialkylphosphine and a halogen molecule.

* * * * *